(12) United States Patent
Matousek et al.

(10) Patent No.: US 7,911,604 B2
(45) Date of Patent: Mar. 22, 2011

(54) SECURITY SCREENING USING RAMAN ANALYSIS

(75) Inventors: Pavel Matousek, Abingdon (GB); Anthony William Parker, Swindon (GB)

(73) Assignee: The Science and Technology Facilities Council, Oxfordshire (GB)

( * ) Notice: Subject to any disclaimer, the term of this patent is extended or adjusted under 35 U.S.C. 154(b) by 267 days.

(21) Appl. No.: 12/085,346

(22) PCT Filed: Nov. 27, 2006

(86) PCT No.: PCT/GB2006/004428
§ 371 (c)(1), (2), (4) Date: May 22, 2008

(87) PCT Pub. No.: WO2007/060467
PCT Pub. Date: May 31, 2007

(65) Prior Publication Data
US 2009/0141271 A1    Jun. 4, 2009

(30) Foreign Application Priority Data

Nov. 25, 2005 (WO) ................ PCT/GB2005/004535
Apr. 5, 2006 (GB) ................................. 0606891.0
Sep. 21, 2006 (GB) ................................. 0618635.7

(51) Int. Cl.
*G01J 3/44* (2006.01)
*G01N 21/65* (2006.01)
(52) U.S. Cl. ...................................................... 356/301
(58) Field of Classification Search .................. 356/301
See application file for complete search history.

(56) References Cited

U.S. PATENT DOCUMENTS

| 3,442,591 A | 5/1969 | Ogura et al. |
| 3,770,350 A | 11/1973 | Stone et al. |
| 4,570,638 A | 2/1986 | Stoddart et al. |
| 4,645,340 A | 2/1987 | Graham et al. |
| 4,714,345 A | 12/1987 | Schrader |
| 4,784,486 A | 11/1988 | Van Wagenen et al. |
| 4,799,786 A | 1/1989 | Gerrard |
| 4,945,239 A | 7/1990 | Wist et al. |
| 5,139,025 A | 8/1992 | Lewis et al. |
| 5,194,913 A | 3/1993 | Myrick et al. |

(Continued)

FOREIGN PATENT DOCUMENTS

CN    1584555 A    2/2005

(Continued)

OTHER PUBLICATIONS

Brenan et al., Volumetric Raman Microscopy Through a Turbid Medium, Journal of Raman Spectroscopy, vol. 27, (1996), pp. 561-570.

(Continued)

*Primary Examiner* — F. L Evans
(74) *Attorney, Agent, or Firm* — Birch, Stewart, Kolasch & Birch, LLP

(57) ABSTRACT

Method and apparatus for screening objects using Raman scattering methods to detect the presence of predefined substances or classes of substances. The predefined substances may be hazardous, toxic, or explosive. Radiation is supplied to an incident region of an object. Scattered light is collected from a collection region on the surface of the object spaced from the incident region. The characteristics of the scattered light include Raman features related to the predefined substances. The Raman features allow the presence, or not, of the predefined substances to be determined.

30 Claims, 7 Drawing Sheets

U.S. PATENT DOCUMENTS

| | | |
|---|---|---|
| 5,261,410 A | 11/1993 | Alfano |
| 5,349,961 A | 9/1994 | Stoddart et al. |
| 5,371,368 A | 12/1994 | Alfano et al. |
| 5,506,678 A | 4/1996 | Carlsen et al. |
| 5,565,982 A | 10/1996 | Lee et al. |
| 5,615,673 A | 4/1997 | Berger et al. |
| 5,625,458 A | 4/1997 | Alfano et al. |
| 5,660,181 A | 8/1997 | Ho et al. |
| 5,752,519 A | 5/1998 | Benaron et al. |
| 5,873,831 A | 2/1999 | Bernstein et al. |
| 5,919,140 A | 7/1999 | Perelman et al. |
| 5,935,062 A | 8/1999 | Messerschmidt et al. |
| 5,999,836 A | 12/1999 | Nelson et al. |
| 6,289,230 B1 | 9/2001 | Chaiken et al. |
| 6,310,686 B1 | 10/2001 | Jiang |
| 6,321,111 B1 | 11/2001 | Perelman et al. |
| 6,352,502 B1 | 3/2002 | Chaiken et al. |
| 6,654,118 B2 | 11/2003 | Bruce |
| 6,681,133 B2 | 1/2004 | Chaiken et al. |
| 6,897,951 B2 | 5/2005 | Womble et al. |
| 6,919,556 B1 | 7/2005 | Laurence |
| 7,219,568 B2 | 5/2007 | Folestad et al. |
| 7,269,245 B2 | 9/2007 | He et al. |
| 7,652,763 B2 | 1/2010 | Matousek et al. |
| 7,697,576 B2 | 4/2010 | Maier et al. |
| 2003/0004419 A1 | 1/2003 | Treado et al. |
| 2003/0018272 A1 | 1/2003 | Treado et al. |
| 2003/0085348 A1 | 5/2003 | Megerle |
| 2003/0120137 A1 | 6/2003 | Pawluczyk |
| 2003/0220549 A1 | 11/2003 | Liu et al. |
| 2004/0051867 A1 | 3/2004 | Brestel et al. |
| 2004/0054270 A1 | 3/2004 | Pewzner et al. |
| 2004/0063214 A1 | 4/2004 | Berlin et al. |
| 2004/0092804 A1 | 5/2004 | Rebec et al. |
| 2004/0133251 A1 | 7/2004 | Altshuler et al. |
| 2004/0186383 A1 | 9/2004 | Rava et al. |
| 2004/0263843 A1 | 12/2004 | Knopp et al. |
| 2005/0010130 A1 | 1/2005 | Morris et al. |
| 2005/0206892 A1 | 9/2005 | Wang et al. |
| 2005/0283058 A1 | 12/2005 | Choo-Smith et al. |
| 2006/0121442 A1 | 6/2006 | Perraut et al. |
| 2006/0158645 A1 | 7/2006 | Maier et al. |
| 2006/0249423 A1 | 11/2006 | Reijonen |
| 2007/0182959 A1 | 8/2007 | Maier et al. |
| 2008/0051645 A1 | 2/2008 | Rebec et al. |
| 2009/0177052 A1 | 7/2009 | Rebec et al. |

FOREIGN PATENT DOCUMENTS

| | | |
|---|---|---|
| EP | 0 781 990 A1 | 7/1997 |
| EP | 1 475 037 A1 | 11/2004 |
| EP | 1 533 607 A2 | 5/2005 |
| GB | 1171689 | 11/1969 |
| GB | 1510827 | 5/1978 |
| GB | 2 244 329 A | 11/1991 |
| JP | 56-22938 A | 3/1981 |
| JP | 8-75652 A | 3/1996 |
| JP | 9-127001 A | 5/1997 |
| JP | 2002-85385 A | 3/2002 |
| JP | 2003-010189 | 1/2003 |
| JP | 2004-248849 | 9/2004 |
| JP | 2004-271220 A | 9/2004 |
| JP | 2004-294150 A | 10/2004 |
| JP | 2005-70009 A | 3/2005 |
| WO | WO-92/15008 A1 | 9/1992 |
| WO | WO-96/06346 A1 | 2/1996 |
| WO | WO-96/26431 A1 | 8/1996 |
| WO | WO-97/22872 A1 | 6/1997 |
| WO | WO-98/00057 A1 | 1/1998 |
| WO | WO 99/32872 A1 | 7/1999 |
| WO | WO 00/07705 A1 | 2/2000 |
| WO | WO-00/16036 A1 | 3/2000 |
| WO | WO-00/20843 A1 | 4/2000 |
| WO | WO 01/22063 A1 | 3/2001 |
| WO | WO-01/39665 A2 | 6/2001 |
| WO | WO 01/52739 A1 | 7/2001 |
| WO | WO 01/57500 A1 | 8/2001 |
| WO | WO 01/60503 A1 | 8/2001 |
| WO | WO-02/07585 A2 | 1/2002 |
| WO | WO 02/061394 A1 | 8/2002 |
| WO | WO-03/023382 A1 | 3/2003 |
| WO | WO-03/041123 A3 | 5/2003 |
| WO | WO 03088070 A1 | 8/2003 |
| WO | WO-03/073082 A1 | 9/2003 |
| WO | WO 03/087793 A1 | 10/2003 |
| WO | WO-2004/031749 A2 | 4/2004 |
| WO | WO 2004/051242 A1 | 6/2004 |
| WO | WO-2004/078044 A1 | 9/2004 |
| WO | WO 2004/078045 A1 | 9/2004 |
| WO | WO 2004/097365 A1 | 11/2004 |
| WO | WO-2004/102186 A1 | 11/2004 |
| WO | WO-2004/111639 A1 | 12/2004 |
| WO | WO-2005/004714 A1 | 1/2005 |
| WO | WO-2005/060622 A2 | 7/2005 |
| WO | WO 2006/061565 A1 | 6/2006 |
| WO | WO 2006/061566 A1 | 6/2006 |
| WO | WO-2006/083316 A2 | 8/2006 |
| WO | WO-2006/091223 A2 | 8/2006 |
| WO | WO-2007/040589 A1 | 4/2007 |
| WO | WO 2008/024288 A2 | 2/2008 |

OTHER PUBLICATIONS

Matousek et al., Subsurface probing in diffusely scattering media using spatially offset Raman spectroscopy Applied Spectroscopy, vol. 59, No. 4, Apr. 2005, pp. 393-400 and 1485.

Myrick et al., Comparison of some fiber optic configurations for measurement of luminescence and Raman scattering, Applied Optics, vol. 29, No. 9, Mar. 20, 1990, pp. 1333-1344.

Schrader et al., Laser-based molecular spectroscopy for chemical analysis raman scattering processes, Pure & Appl. Chem., vol. 69, No. 7, 1997, pp. 1451-1468.

Butterfield, Through-package applications of Raman spectroscopy for nondestructive identification of product, American Laboratory News, Nov. 1999, p. 14.

Matousek, Deep non-invasive Raman spectroscopy of living tissue and powders, Chemical Society Review, vol. 36, 2007, pp. 1292-1304.

Matousek, Raman Signal Enhancement in Deep Spectroscopy of Turbid Media, Applied Spectroscopy, vol. 61, No. 8, 2007, pp. 845-854.

Matousek et al., Prospects for the diagnosis of breast cancer by noninvase probing of calcifications using transmission Raman spectroscopy, Journal of Biomedical Optics, vol. 12, No. 2, Mar./Apr. 2007, pp. 024008-1-024008-8.

Matousek et al., Non-invasive probing of pharmaceutical capsules using transmission Raman spectroscopy, Journal of Raman Spectroscopy, vol. 38, 2007, pp. 563-567.

Matousek et al., Bulk Raman Analysis of Pharmaceutical Tablets, Applied Spectroscopy, vol. 60, No. 12, 2006, pp. 1353-1357.

Williams et al., Evaluation of drug physical form during granulation, tabletting and storage, International Journal of Pharmaceutics, vol. 29, (2004), pp. 29-39.

Wang et al., Direct assay and shelf-life monitoring of aspirin tablets using Raman spectroscopy, Journal of Pharmaceutical and Biomedical Analysis, vol. 16, (1997), pp. 87-94.

Dyrby et al., Chemometric Quantitation of the Active Substance (Containing C=N) in a Pharmaceutical Tablet Using Near-Infrared (NIR) Transmittance and NIR FT-Raman Spectra, vol. 56, No. 5, 2002, pp. 579-585.

Johansson et al., Characterization of different laser irradiation methods for quantitative raman tablet assessment, Journal of Pharmaceutical and Biomedical Analysis, vol. 39, (2005), pp. 510-516.

Bell et al., Composition profiling of seized ecstasy tablets by Raman spectroscopy, Analyst, vol. 125, 2000, pp. 1811-1815.

Hausman et al., Application of on-line Raman spectroscopy for characterizing relationships between drug hydration state and tablet physical stability, International Journal of Pharmaceutics, vol. 299, (2005), pp. 19-33.

Szostak et al., Quantitative determination of acetylsalicylic acid and acetaminophen in tablets by FT-Raman spectroscopy, Analyst, vol. 127, 2002, pp. 144-148.

Breitenbach et al., Pharmaceutical Research, Confocal Raman-Spectroscopy: Analytical Approach to Solid Dispersions and Mapping of Drugs, vol. 16, No. 7, 1999, pp. 1109-1113.

Taylor et al., Journal of Pharmaceutical, Evaluation of Solid-State Forms Present in Tablets by Raman Spectroscopy, vol. 89, No. 10, Oct. 2000, pp. 1342-1353.

Matousek et al., Fluorescence background suppression in Raman spectroscopy using combined Kerr gated and shifted excitation Raman difference techniques, Journal of Raman Spectroscopy, vol. 33, No. 4, Apr. 2002, pp. 238-242.

Kincade, Optical diagnostics image tissues and tumors, Laser Focus World, vol. 32, No. 2, Feb. 1996, 5 page printout.

Hasegawa, Detection of minute chemical signals by principal component analysis, Trends in Analytical Chemistry, vol. 20, No. 2, 2001, pp. 53-64.

Wu et al., Three dimensional imaging of objects embedded in turbid media with fluorescence and Raman spectroscopy, Applied Optics, vol. 34, No. 18, Jun. 20, 1995, pp. 3425-3430.

Ma et al., Rapid Micro-Raman Imaging using Fiber-Bundle Image Compression, Applied Spectroscopy, vol. 51, No. 12, 1997, pp. 1845-1848.

Dunsby et al., Techniques for depth-resolved imaging through turbid media including coherence-gated imaging, Journal of Physics D. Applied Physics, vol. 36, (2003), pp. R207-R227.

Matousek et al., "Subsurface probing in diffusely scattering media using spatially offset Raman spectroscopy," Applied Spectroscopy, vol. 59, No. 4, 2005, pp. 393-400.

Schrader et al., "Die Intensität des Ramanspektrums polykristalliner Substanzen," Fresenius Journal of Analytical Chemistry, vol. 225, 1967, pp. 230-247.

Carter, et al., Raman spectroscopy for the in situ identification of cocaine and selected adulterants, Applied Spectroscopy, The Society for Applied Spectroscopy, Baltimore, US vol. 54, No. 12, Dec. 2000, pp. 1876-1881.

Coates, Molecular spectroscopy workbench new technologies for process analytical and quality control applications: Compact Raman, Spectroscopy, Advanstar Communications, US, vol. 21, No. 2, Feb. 2006, pp. 68-74.

Das et al., Time-resolved fluorescence and photon migration studies in biomedical and model random media, Rep. Prog Phys., vol. 60, pp. 227-292 (1997).

Draper et al., Novel Assessment of Bone Using Time-Resolved Transcutaneous Raman Spectroscopy, Journal of Bone and Mineral Research, vol. 20, No. 11, 2005, pp. 1968-1972.

Dukor et al., A new, Non-Destructive Method for Analysis of Clinical Samples with FT-IR Microspectroscopy., Breast Cancer Tissue as an example, Cellular and Molecular Biology, vol. 44, No. 1, (1998), pp. 211-217.

Eliasson et al., Non-invasive detection of cocaine dissolved in beverages using displaced Raman spectroscopy Analytica Chimica Acta, Elsevier, Amsterdam NL, vol. 607, No. 1, Nov. 19, 2007, pp. 50-53.

Eliasson et al., Non-invasive detection of concealed liquid explosives using Raman spectroscopy, Analytical Chemistry Nov. 1, 2007, vol. 79, No. 21, pp. 8185-8189.

Everall et al., Photon Migration in Raman Spectroscopy, Applied Spectroscopy, vol. 58, No. 5, 2004, pp. 591-597.

Everall et al., Picosecond Time-Resolved Raman Spectroscopy of Solids: Capabilities and Limitations for Fluorescence Rejection and the Influence of Diffuse Reflectance, Applied Spectroscopy, vol. 55, No. 12, 2001, pp. 1701-1708.

Haka et al., Identifying Microcalification in Benign and Malignant Breast Lesions by Probing Differences in Their Chemical Composition Using Raman Spectroscopy, Cancer Research, vol. 62, Sep. 15, 2002, pp. 5375-5380.

Haka et al., Diagnosing breast cancer by using Raman spectroscopy, PNAS, vol. 102, No. 35, Aug. 30, 2005, pp. 12371-12376.

Hanlon et al., Prospects for in vivo Raman spectroscopy, Phys. Med. Bio., vol. 45, pp. R1-R59, 2000.

Lewis et al., Raman spectroscopic studies of explosive materials: towards a fieldable explosives detector, Spectrochimica Acta, Part A (Molecular Spectroscopy), Elsevier UK, vol. 51A, No. 12, pp. 1985-2000, Nov. 16, 1995.

Matousek et al., Depth Profiling in Diffusely Scattering Media Using Raman Spectroscopy and Picosecond Kerr Gating, Applied Spectroscopy, vol. 59, No. 2, 2005, pp. 200-205.

Matousek et al., Flurorescence suppression in resonance Raman spectroscopy using a high-performance picosecond Kerr gate, Journal of Raman Spectroscopy, vol. 32, 2001, pp. 983-988.

Matousek et al., Noninvasive Raman Spectroscopy of human tissue in vivo, Applied Spectroscopy, The Society for Applied Spectroscopy, Baltimore, US, vol. 60, No. 7, Jul. 2006, pp. 758-763.

Matousek et, al. Efficient Rejection of Fluorescene from Raman Spectra Using Picosecond Kerr Gating, Applied Spectroscopy, vol. 53, No. 12, 1999, pp. 1485-1489.

Matousek, et al., "Numerical Simulations of Subsurface Probing in Diffusely Scattering Media Using Spatially Offset Raman Spectroscopy", Applied Spectroscopy, vol. 59, No. 12, pp. 1485-1492, May 3, 2005.

Matousek, Inverse spatially offset raman spectroscopy for deep noninvasive probing of turbid media, Applied Spectroscopy, The Society for Applied Spectroscopy, Baltimore, US, vol. 60, No. 11, Nov. 1, 2006, pp. 1341-1347.

Morris et al., Kerr-gated time-resolved Raman spectroscopy of equine cortical bone tissue, Journal of Biomedical Optics, vol. 10, No. 1, (Jan./Feb. 2005), pp. 014014-1-01401-7.

Niemczyk, et al., Quantitative Determination of Bucindolol Concentration in Intact Gel Capsules Using Raman Spectroscopy, Department of Chemistry, University of New Mexico, Albuquerque, New Mexico 87131, pp. 2762-2765, Analytical Chemistry, 1998.

Schulmerich et al., Subsurface Raman Spectroscopy and Mapping Using a Globally Illuminated Non-Confocal Fiber-Optic Array Probe in the Presence of Raman Photon Migration, Applied Spectroscopy, vol. 60, No. 2, 2006, pp. 109-114.

Schulmerich et al., Transcutaneous fiber optic Raman spectroscopy of bone using annular illumination and a circular array of collection fibers, Journal of Biomedical Optics, vol. 11, No. 6, Nov./Dec. 2006, PP060502-1.

Schulmerich et al., Transcutaneous Raman spectroscopy of bone tissue using a non-confocal fiber optic array probe, Proc. of SPIE, vol. 6093, pp. 609300-1, 609300-7, Feb. 27, 2006.

Shafer-Peltier et al., Raman microspectroscopic model of human breast tissue: implications for breast cancer diagnosis in vivo, Journal of Raman Spectroscopy, vol. 33, Issue 7, 2002, pp. 552-563.

Stone et al., Near-infrared Raman spectroscopy for the classification of epithelial pre-cancers and cancers, Journal of Raman Spectroscopy, vol. 33, 2002, pp. 546-573.

Sun et al., Basic calcium phosphate crystals stimulate the endocytotic activity of cells-inhibition by anti-calcification agents, BBRC, vol. 312, (2003), pp. 1053-1059.

Weng et al., FTIR fiber optics and FT-Raman spectroscopic studies for the diagnosis of cancer, American Clinical Laboratory, vol. 19, Aug. 2000, p. 20.

J. Klosowski et al., "Experiments on Raman versus Primary Light scattering fluxes From Pressed Discs", Journal of Raman Spectroscopy, vol. 8, No. 3, pp. 169-171, 1979.

B. Schrader and G. Bergman, "Die Intensität des Ramanspektrums polykristalliner Substanzen", Fresenius Journal of Analytical Chemistry, vol. 225, pp. 230-247, 1967.

SECURITY SCREENING USING RAMAN ANALYSIS

FIELD OF THE INVENTION

The present invention relates to methods and apparatus for screening objects to detect the presence of predefined substances. In particular, the present invention relates to Raman scattering methods for detecting predefined substances in envelopes, packages, or carried about the person. The predefined substances may be substances which are hazardous, toxic, or explosive.

DISCUSSION OF THE PRIOR ART

Recent events and a perceived increased threat from terrorist activities have resulted in an increased need to be able to identify explosives and other hazardous materials that might be carried by individuals, or sent through the post.

The demands on a technique for identifying hazardous materials are high. The technique must be fast, non-invasive, and the results should be available in seconds, be easy to interpret, and be accurate.

For items carried about the person, or items sent through the post, the identification technique must be able to detect the hazardous material through covering layers such as clothing or packaging.

Conventional security scanners used at airports or to scan parcels and mail use X-ray sources. These sources require a high voltage, in the order of 100 kV, to generate the X-rays, and enable imaging through thick items like suitcases. The scanner must also comprise shielding to prevent operators from being exposed to excessive doses of X-ray radiation. The resulting scanners tend to be large.

Additionally, although X-ray scanners can readily distinguish between metals, plastics and fabrics etc. it is much more difficult to distinguish between for example, food and explosives.

Advanced X-ray scanning techniques use the X-ray diffraction method in which the X-ray radiation is scattered by the crystalline structure of a material. The diffraction spectra is measured and compared with reference spectra. For example, different explosives may have different spectra, and by searching for characteristic spectra, explosives can be detected. However, such analysis requires bulky X-ray equipment and the analysis may also be time consuming.

Other imaging techniques using radiation of different frequencies have also been investigated. For example, infra-red imaging can be used to detect objects carried about a person. Infra-red techniques generally rely on imaging heat generated by the human body and looking for irregularities in the resulting image. However, the imaging of objects where no body heat source is present is difficult, and moreover, the ability to distinguish between, for example, food and explosives using infra-red technology is highly complex.

It would be desirable to provide methods and apparatus for scanning the contents of packages, and accurately determining the composition of the contents. For example, it would desirable to be able to distinguish hazardous materials and explosives from their packaging and other non-hazardous materials, such as food or clothing.

SUMMARY OF THE INVENTION

Accordingly, the present invention provides a method of screening an object to identify the presence or otherwise of predefined substances, in particular the bulk or interior, or an interior portion of an object, by directing incident radiation at a first surface, surface region, area or portion of the object, collecting forward scattered radiation from a second surface, surface region, area or portion of the object, and detecting Raman radiation, arising from Raman scattering of said incident radiation within said object, in the collected radiation. This may be applied to the screening of mail, for example, in a mail distribution centre. Alternatively, the screening process may be applied to clothing worn by person's entering high security areas, such as those at airports.

Particular embodiments of the present invention provide a method of screening an object to identify the presence or otherwise of one or more predefined substances, the method comprising the steps of: supplying incident radiation to an incident region on a surface of said object; detecting Raman scattered light from a collection region on a surface of said object, the collection region being spaced from the incident region; comparing the Raman scattered light to information related to said predefined substances; and determining the presence or otherwise of said one or more predefined substances in said object. The predefined substances may also be classes of substances, such as nitrides or amine groups.

The incident region is on a first surface of the object, and the collection region may be on a second surface of the object in confronting relationship to said first surface. The incident region on the first surface and the collection region on the second surface may be aligned to an axis of the object.

Alternatively, or in combination with having the incident region and collection regions on opposing surfaces, the incident region and the collection region may be on the same surface, or the same side of the object.

The information related to the predefined substances may be stored in a database. The information may relate to characteristic features in a Raman spectrum of the predefined substance. In particular, the information may be the frequency shift at which maxima or peaks in the Raman spectra occur.

The object may be an envelope, package, or garment of clothing.

The above described method is particularly useful for detecting hazardous, toxic, or explosive substances, but is is not limited to these. The substances may instead be illegal substances such as drugs of abuse, or counterfeit drugs.

The present invention also provides screening apparatus for identifying the presence or otherwise of predefined substances in an object, the apparatus comprising: illumination optics arranged to direct incident radiation at an incident region on the surface of said object; collection means for collecting Raman scattered light from a collection region on the surface of said object, the collection region being spaced from the incident region; a comparator for comparing the Raman scattered light to information related to said predefined substances; and an analyser for determining the presence or otherwise of said one or more predefined substances in said object. The predefined substances may also be classes of substances, such as nitrides or amine groups.

The incident region is on a first surface of the object, and the collection region may be on a second surface of the object in confronting relationship to said first surface. The incident region on the first surface and the collection region on the second surface may be aligned to an axis of the object.

Alternatively, or in combination with having the incident region and collection regions on opposing surfaces, the incident region and the collection region may be on the same surface, that is, a surface on the same side of the object.

The screening apparatus may also include a database for storing the information related to the predefined substances.

The object may be an envelope, package, or garment of clothing.

The above described apparatus is particularly useful for detecting hazardous, toxic, or explosive substances, but is not limited to these. The substances may instead be illegal substances such as drugs of abuse, or counterfeit drugs.

BRIEF DESCRIPTION OF THE DRAWINGS

Embodiments of the present invention will now be described with reference to the drawings, of which.

DETAILED DESCRIPTION OF THE PREFERRED EMBODIMENTS

When light is scattered from a molecule most photons are elastically scattered. However, a small fraction of light is scattered at optical frequencies different from, and usually lower than the frequency of the incident photons. This scattering process is termed the Raman effect. Raman scattering occurs due to a change in the vibrational, rotational or electronic energy of a molecule. The Raman effect is widely used in chemical spectroscopy.

Since the Raman effect is particularly weak, conventional Raman spectroscopy is typically used only for analysis of the surface of turbid samples. Unfortunately, conventional Raman techniques are particularly susceptible to interference from luminescence and fluorescence from the illuminated surface. A number of techniques have been specifically developed using alternative geometries, and spatial offsets to address the problem of fluorescence. These are transmission Raman spectroscopy, and spatially offset Raman spectroscopy which are described in detail below. These techniques are particularly suited to non-destructive testing of objects to find hazardous materials. In particular, the objects may be packages or envelopes sent via the postal services. Alternatively, the techniques may be used to identify hazardous substances carried under clothing by a person.

Transmission Raman
Technique

Figure 1:
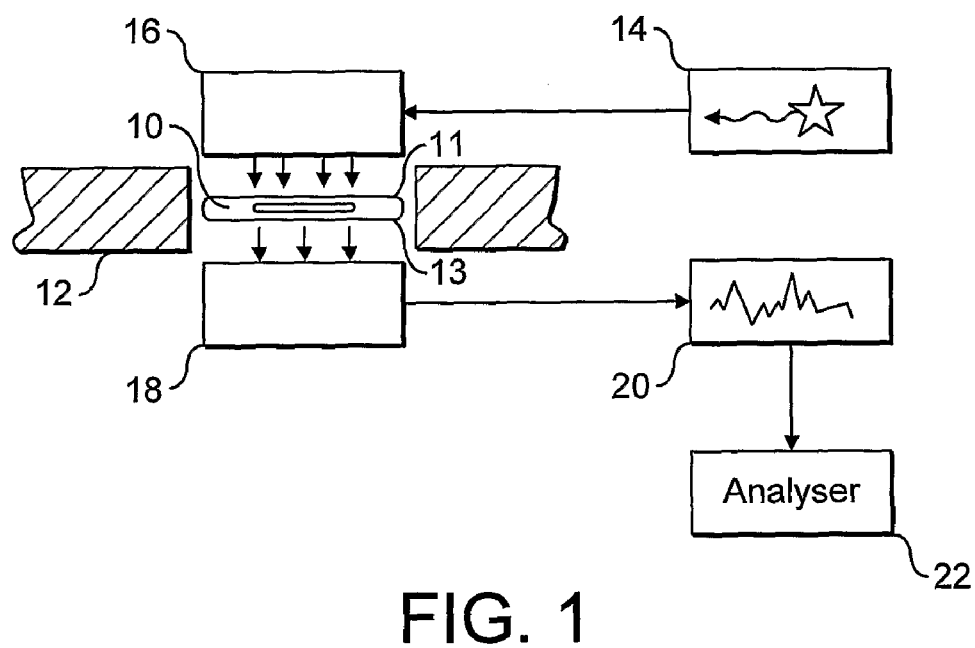
FIG. 1 is a schematic illustration of an arrangement for performing transmission Raman analysis on an envelope or package.

Referring now to FIG. 1 there is shown a package 10, such as a parcel or envelope, such that at least part of each of the upper 11 and lower 13 surfaces of the package are exposed. The package may be held on carrier 12 or may pass along a conveyor or mail inspection line. Light generated by a laser 14 is directed to illumination optics 16 above the carrier which cause the upper surface of the package to be exposed to the laser light. Receiving optics 18 are disposed below the carrier arranged to receive light scattering out of the lower surface of the package. This light is directed to a spectrographic detector 20, and results from the spectrographic detector 20 are passed to a computer implemented analyser 22.

Suitable wavelengths for the incident laser light are around the near infrared part of the spectrum, for example at 827 nm with a laser power of about 55 mW as used in the example discussed below. Further details of suitable optical arrangements for the illumination, receiving and detection optics can be found in the "Experimental Example" section below. However, any other suitable wavelengths may be used.

Some of the photons of the incident laser light undergo Raman scattering in the package. The production of Raman photons having particular wavelengths depends on the chemical structure of the package and its contents. For example, particular hazardous or explosive materials can be deduced by analysing the scattered Raman photons and comparing to the spectra of known hazardous substances and explosives. The computer analyser 22 uses the spectral results from the detector 20 in this way to deduce if the package or its contents comprise hazardous substances.

Most of the Raman photons backscatter towards the illumination optics. Almost all of the backscattered Raman photons are produced close to the illuminated upper surface of the package, and so only allow properties of that surface region to be deduced.

Raman photons also scatter forwards and emerge from the lower surface of the package. Although the number of forward scattered Raman photons is small compared with the number of backscattered photons, these forward scattered photons originate from a relatively even range of depths throughout the package, and so allow bulk properties of the package as a whole to be deduced. The spectrographic detector could take a variety of known forms such as a conventional spectrograph, a Fourier Transform spectrograph, or one or more filters in conjunction with one or more photo detectors.

Figure 2:
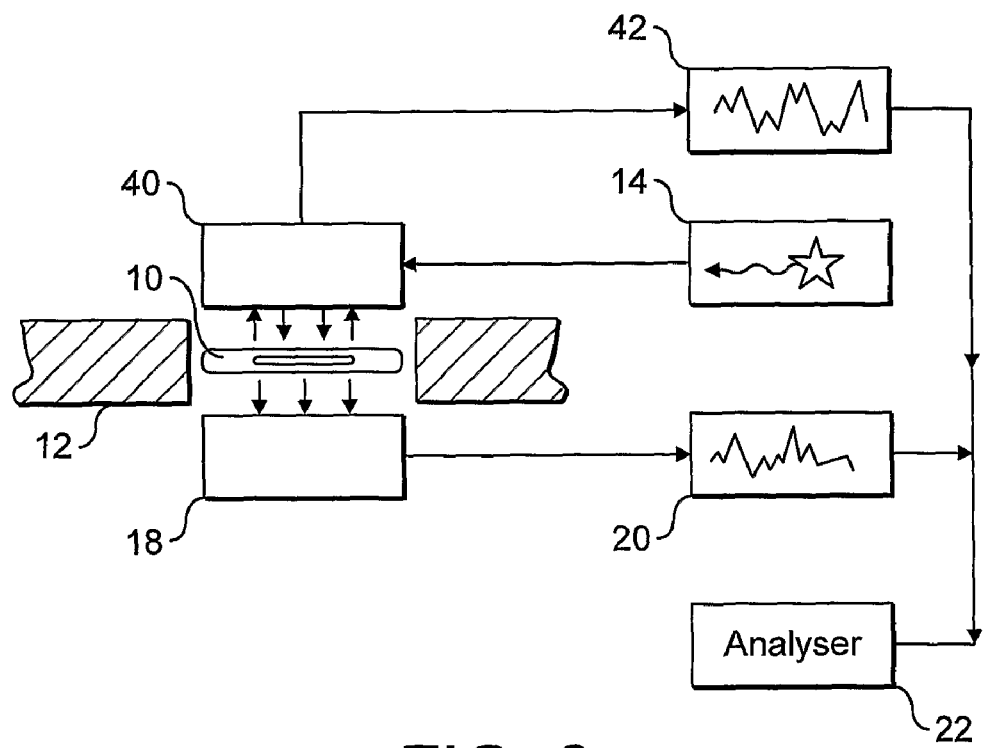
FIG. 2 is a schematic illustration of an arrangement for performing Raman analysis using forward scattered and back-scattered photons from an envelope or package.

In addition to the above described embodiments having detection optics placed on the opposite side of the package to the illumination optics, FIG. 2 shows an alternative arrangement in which the illumination optics 40 also comprises receiving optics to collect backscattered Raman photons. These are passed to a separate spectrographic detector 42, or alternatively to the detector 20 used to detect forward scattered photons, for detection and subsequent analysis. In this way, forward scattered and back scattered photons may be detected and analysed at the same time, or at different times.

In the embodiments illustrated in FIGS. 1 and 2 the package is generally flat and is shown illuminated on one side with at least one set of detection optics arranged on the opposite side of the package. However, it is not necessary to place the illumination and receiving optics in confrontational relationship in order to derive bulk properties of the package using a transmission geometry, although this may frequently be a preferred configuration for evenly distributed sampling of the package. Generally, however, the surface of the package illuminated by the illumination optics should at least be separated or spaced from the surface from which scattered light is received by the receiving optics.

The above described embodiment is not limited to screening packages but may also be used to screen clothes worn by a wearer. For example, a person's clothing may be screened to identify if hazardous materials are concealed in the lining of clothes. This technique allows the composition of such a hidden object to be determined in a non-destructive manner.

Numerical Modelling

A Monte Carlo model was used to simulate the transport of illumination photons and Raman photons scattering within a turbid medium such as a hazardous material enclosed in an envelope. The model was used to calculate the relative intensities of backscattered and forward scattered Raman photons as a function of their depth within the turbid medium. Briefly, both the elastically (illumination) and non-elastically (Raman) scattered photons were individually followed as they propagated through the medium in random walk-like fashion in three-dimensional space. A simplified assumption was made that in each step a photon propagated in a straight line over a distance t and thereafter its direction was fully randomised at the next scattering event. Although this picture is simplistic from the standpoint of individual scattering events, photons propagating through a turbid medium typically have to undergo a number of scattering events (e.g. 10-20) before their original direction of propagation becomes fully scrambled. This is due to the fact that individual scattering events are often strongly biased towards the forward direction. However, it has been shown that for large propagation distances such as those pertinent to the bulk analysis of objects of interest here, the individual multiple scattering events can be approximated as a single composite event occurring over the 'randomisation length' t (Matousek P. et al., Applied Spectroscopy 59, p 1485, 2005). This simplified assumption enables analysis of large propagation distances with modest computational expense.

The propagation distance, t, over which the photon direction is randomised, can be crudely approximated as the transport length of the scattering medium (lt) (Brenan C. and Hunter I., Journal of Raman Spectroscopy 27, p 561, 1996) which is defined in a similar manner as the average distance photons must travel within the sample before deviating significantly from their original direction of propagation. The transport length is typically an order of magnitude longer than the mean free scattering length (ls) of photons in the medium; the precise relation is $ls=(1-g)lt$, where g is the anisotropy for the individual scattering event. In the present model it was also assumed that the wavelength of light propagating through the medium was substantially shorter than the scattering length ls.

Figure 3:
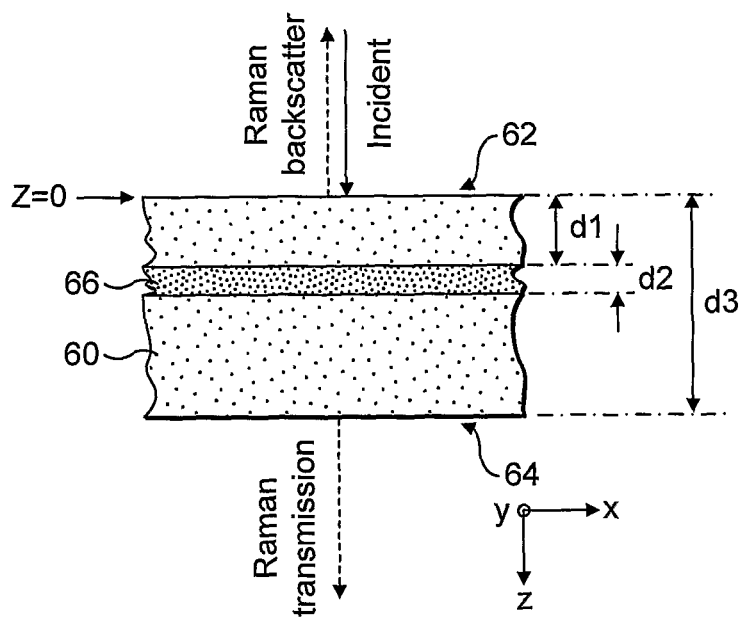
FIG. 3 is an illustration of the geometry of a sample comprising an intermediate layer, as used in a Monte Carlo scattering simulation.

The modelled sample 60 is illustrated in FIG. 3. The sample was considered to extend to infinity in x and y directions, with an air-medium interface located at the top surface 62 z=0 and bottom surface 64 z=d3, where z is a Cartesian coordinate normal to the interface plane. The sample was modelled as a uniform turbid medium apart from an intermediate-layer 66 having a different Raman signature to represent a heterogenous impurity, the intermediate layer having a thickness d2 with a top surface located at depth d1. The overall modelled sample thickness was d3 (d3>=d1+d2). That is, the bulk sample medium was located at depths z1 such that d1>z1>0 and d3>z1>(d1+d2), and the intermediate layer of a different Raman signature at depths z2 such that d1+d2>z2>d1. In the simulations reported herein the parameters d2 and d3 were fixed at 0.5 mm and 4 mm respectively, and d1 was varied from 0 to 3.5 mm to represent different depths of the interlayer 66 within the bulk of the sample 60.

The model assumed that all the illumination photons were first placed at a depth equal to the transport length lt and symmetrically distributed around the origin of the co-ordinate system x, y. The beam radius of the incident light r was 3 mm and the beam was given a uniform 'top-hat' intensity profile with all the photons having equal probability of being injected into the sample at any point within its cross-section. In the model, the Raman light was collected firstly at the top sample surface 62 from the illumination area of the incident light, and separately on the opposite side of the sample 64 symmetrically around the projection axis of the top collection/laser illumination area.

The laser beam photons were propagated through the medium by translating each individual photon in a random direction by a step t. At each step there was a given probability that the photon would be converted to a Raman photon. The absorption of photons was assumed to be insignificant in this simulation. This parameter is expressed as optical density for the conversion of laser beam photons to Raman light. That is, for example, an optical density (OD) of 1 or 2 per 1 mm corresponds to the 10-fold or 100-fold decrease of the number of illumination photons through conversion to Raman photons, respectively, passing through an overall propagation distance of 1 mm. The optical density accounting for the conversion of illumination photons into Raman photons was set to 0.01 per mm. Although this value is higher than that of real conversion, it only affects the absolute number of Raman photons, and not the spatial dependencies of concern. When an illumination photon is converted into a Raman photon the layer where this occurred is identified and recorded. Raman photons are propagated in the same fashion as illumination photons. A dominant mechanism for photon escape exists at the sample-to-air interfaces 62, 64, as none of the laser photons emerging from the sample at these interfaces return back into the sample and are effectively lost from the migration process. A Raman photon emerging at the top or bottom interface within the collection aperture of radius 3 mm centred on the axis of the laser beam are separately counted as detected Raman photons. Any photon emerging from the sample is eliminated from further calculations.

The numerical code for putting the model into effect was written in Mathematica 5.0 (Wolfram Research). 100,000 simulated photons were propagated, each over an overall distance of 40 mm which is in line with typical migration times observed in Raman spectroscopy in the absence of absorption. The step size used was t=0.2 mm (i.e. 200 steps was used). This corresponds to a sample formed from a powder having particle sizes of 10 and 20 μm diameter for the anisotropy of 0.9 and 0.95, respectively. It was checked that upon these times the vast majority of photons were lost at sample-to-surface interfaces. This process was repeated 50-times. Hence, the overall number of propagated photons was $10^6$ with the total number of steps considered being approximately $10^9$. All the detected Raman photons in these repeated runs were summed up.

Figure 4:
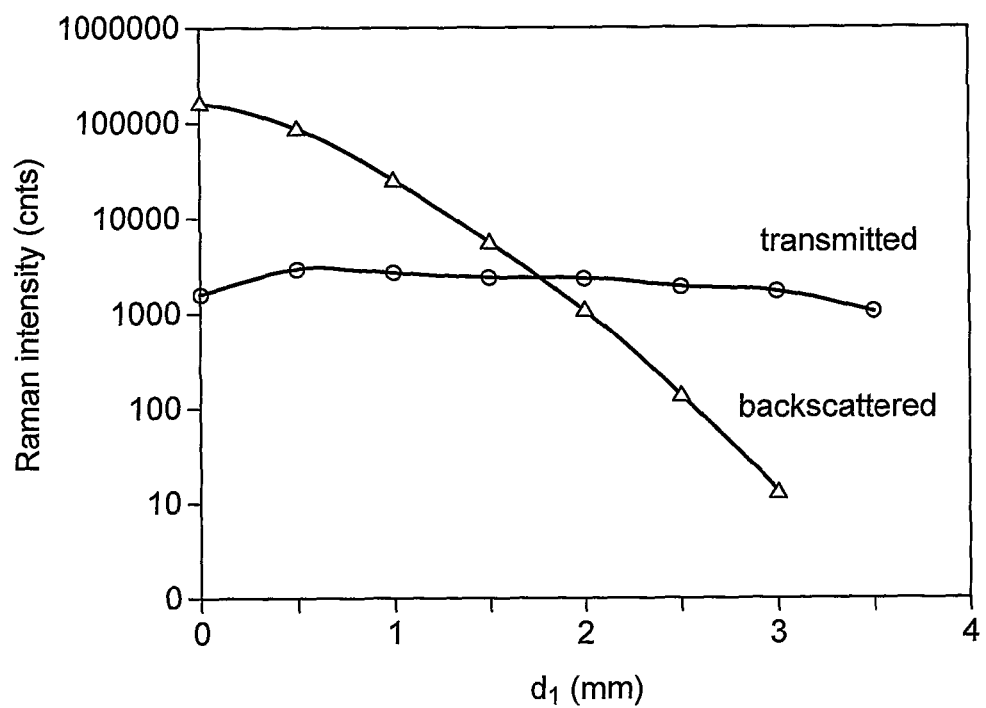
FIG. 4 shows graphs of transmitted and back-scattered Raman radiation originating in the intermediate layer shown in FIG. 3, dependent upon the depth of the layer $d_1$.

The number of Raman photons originating in the intermediate layer 66 and collected as backscattered photons at the upper surface 62, and transmitted photons at the lower surface 64, are shown in FIG. 4. The graphs show the number of backscattered and transmitted photons for eight different depths d1 of the intermediate layer 66 ranging from at the top surface where d1=0 mm to at the bottom surface where d1=3.5 mm.

From FIG. 4 it is clear that the collection of Raman photons in backscattering geometry even from an aperture as large as 6 mm in diameter leads to an extremely strong bias towards the surface layers of the sample. The repositioning of the 0.5 mm thick intermediate layer from the illuminated surface to a depth of 1.5 mm reduces the Raman backscatter intensity by 97%. In most practical applications the Raman signal. will already have become swamped by the Raman or fluorescence signal originating from the surface region of the medium. At a depth of 3 mm the Raman signal originating from the intermediate layer has fallen by 4 orders of magnitude from its original level at the zero depth. On the other hand the dependence of the intensity of transmitted Raman photons exhibits only a weak dependence on the position of the intermediate layer within the sample. As the intermediate layer is moved between depths of 0 mm and 3.5 mm the corresponding Raman signal varies only by a factor of about 2. The absolute intensity of the Raman signal from the intermediate layer is only about 20-times lower than that of the bulk medium making detection relatively straightforward. Therefore the transmission geometry clearly provides a more representative sampling of the bulk of the sample interior than the conventional backscattering geometry, while permitting a satisfactory sensitivity.

For backscattering geometry, the model also reveals that an increase in sample thickness from 1 mm to 4 mm results in a 58% increase of the Raman signal detected in the backscattering geometry. In simplistic terms, this could be wrongly interpreted as extra Raman photons (amounting to 37% of the overall Raman signal observed for 4 mm package) being produced in the extra 3 mm thickness added to the top 1 mm sample layer. However, the model of a 4 mm-thick sample indicates that 88% of Raman signal originates in the top 1 mm layer and only 12% originates within the remaining 3 mm of sample thickness. The extra 3 mm of material not only contributes with extra production of Raman photons but also reduces the loss of Raman photons originated within the 1 mm-layer at the lower surface 64. Thus the increase in backscattered Raman photons through the addition of a further 3 mm of sample is also accomplished by returning Raman photons originating near the upper surface back towards the upper surface from where they may emerge and be collected. In the same way, some illumination photons are scattered back towards the upper surface 62 allowing them to originate still more Raman photons within the top 1 mm layer.

Experimental Example

In an experimental arrangement, the sample package was a standard white envelope with sugar as the contents. A continuous wave laser beam generated from a temperature stabilised diode laser operating at 827 nm was used to illuminate the sample. The beam was spectrally purified using two 830 nm bandpass filters to remove any amplified spontaneous emission components from the spectrum. The filters were slightly tilted to improve their transmission at 827 nm. The purified laser beam had a power of 55 mW at the sample, and the beam diameter was around 3 mm.

Raman scattered light was collected from the opposing side of the sample using a 1.2 f-number lens with a focal length of 60 mm. The scattered light was collimated and passed through a 50 mm diameter holographic notch filter (830 nm, Kaiser Optical Systems, Inc) to suppress the elastically scattered component of light. The filter was also slightly tilted to optimise suppression for the 827 nm wavelength. A second lens, identical to the first, was then used to image, with a magnification of 1:1, the sample surface onto the front face of an optical fibre probe. The laser illumination spot was imaged in such a way that it coincided with the centre of the probe axis.

The fibre probe was comprised of 22 fibres placed tightly packed at the centre of the probe. The fibres were made of silica with a core diameter of 200 μm, cladding diameter of 230 μm and numerical aperture of 0.37. Sleeves were stripped on both ends for tighter packing of the fibres. The Raman light was propagated through the fibre systems with a length of about 2 m to a linear fibre end oriented vertically and placed in the input image plane of a Kaiser Optical Technologies Holospec f#=1.4 NIR spectrograph with its slit removed. In this orientation the fibres themselves acted as the input slit of the spectrograph. Raman spectra were collected using a deep depletion thermoelectrically cooled CCD camera (Andor technology, DU420A-BR-DD, 1024×256 pixels) by binning the signal from all the 22 fibres into one Raman spectrum. Hence, the Raman spectra were not corrected for the variation of detection system sensitivity across the detected spectral range. The acquisition time for the experiments was 10 seconds. However, it is expected that this time may be reduced.

Figure 5A:
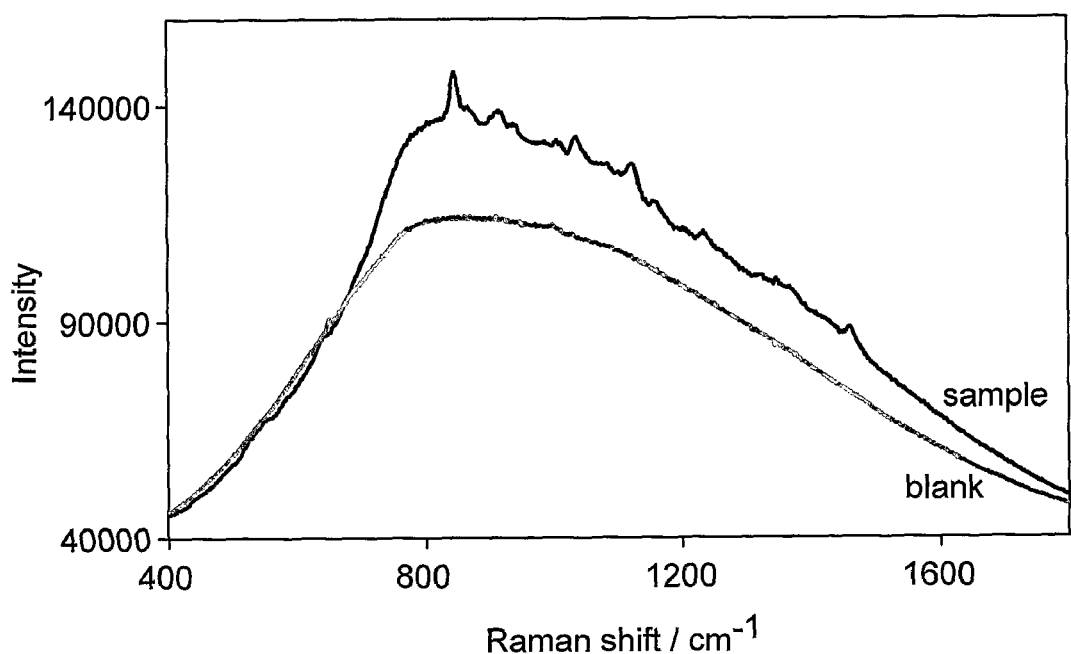
FIG. 5a shows transmission Raman spectra obtained from an empty white envelope and a white envelope containing sugar.
Figure 5B:
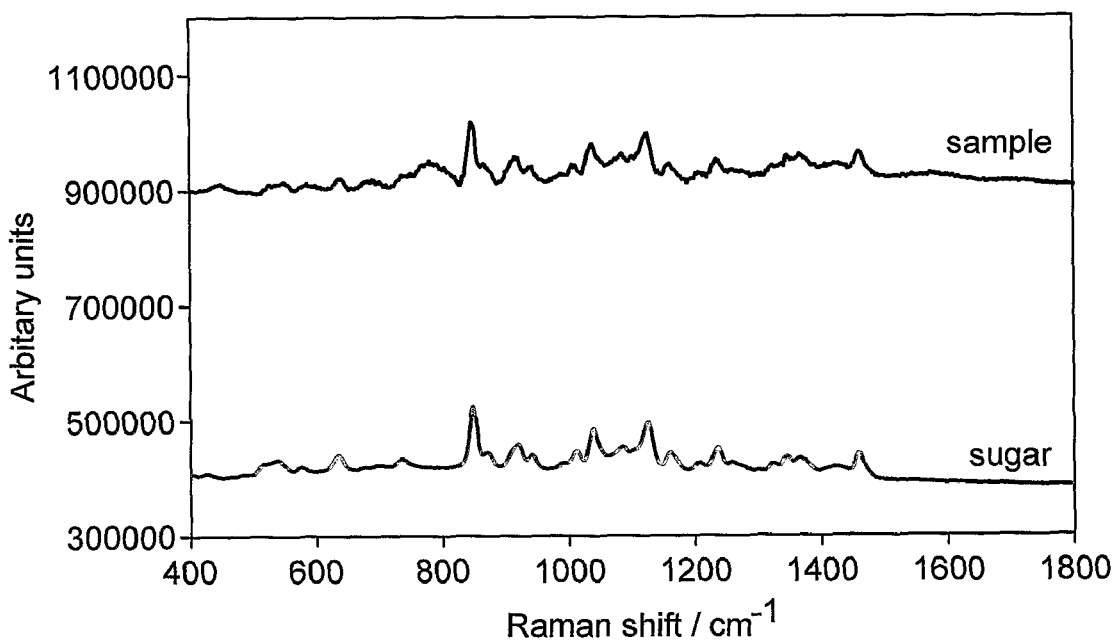
FIG. 5b shows the data of FIG. 5a corrected against the empty envelope and compared to a reference sample of sugar.

Results obtained using this experimental arrangement are shown in FIGS. 5 and 6. FIGS. 5a and 5b show spectra obtained from a white envelope. FIG. 5a shows two sets of data. The first set of data is labelled "blank", and shows the Raman spectrum obtained from an empty white envelope. The second spectrum in FIG. 5a shows that obtained from the sugar-containing envelope. The empty envelope produces significant fluorescence but additional features are clearly visible in the spectra. FIG. 5b shows a background corrected sample spectrum labelled "sample". In this case the fluorescence from the envelope has been subtracted. Also in FIG. 5b is a spectrum obtained from a reference sample of sugar only. Comparing the peaks and features in the spectra of the background corrected sample and the sugar only sample shows that sugar is easily identifiable as present in the envelope.

Figure 6A:
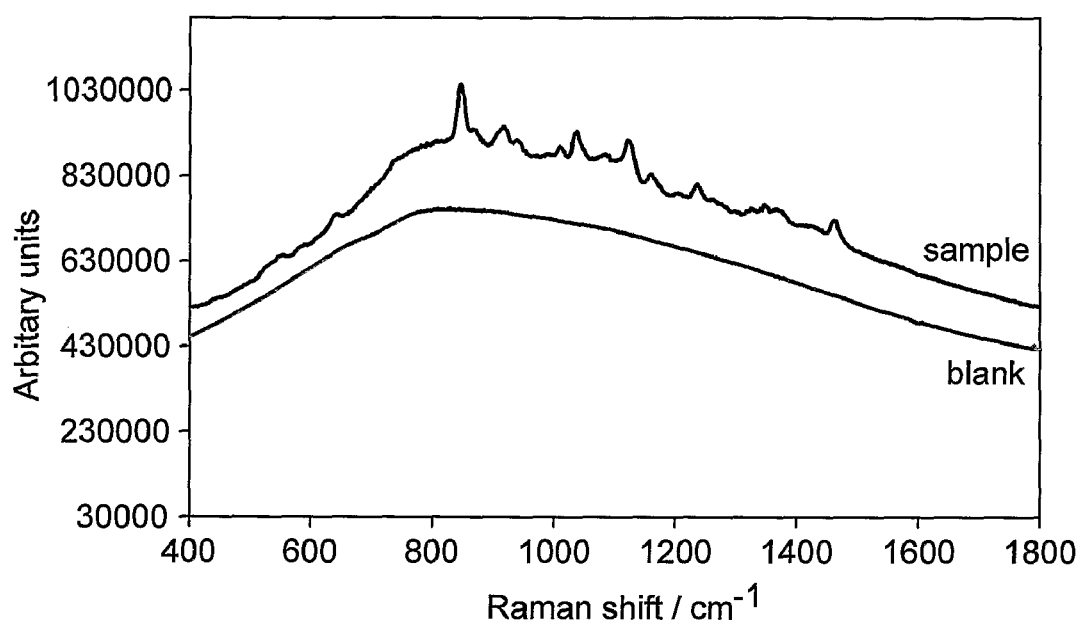
FIG. 6a shows transmission Raman spectra obtained from an empty brown envelope and a brown envelope containing sugar.
Figure 6B:
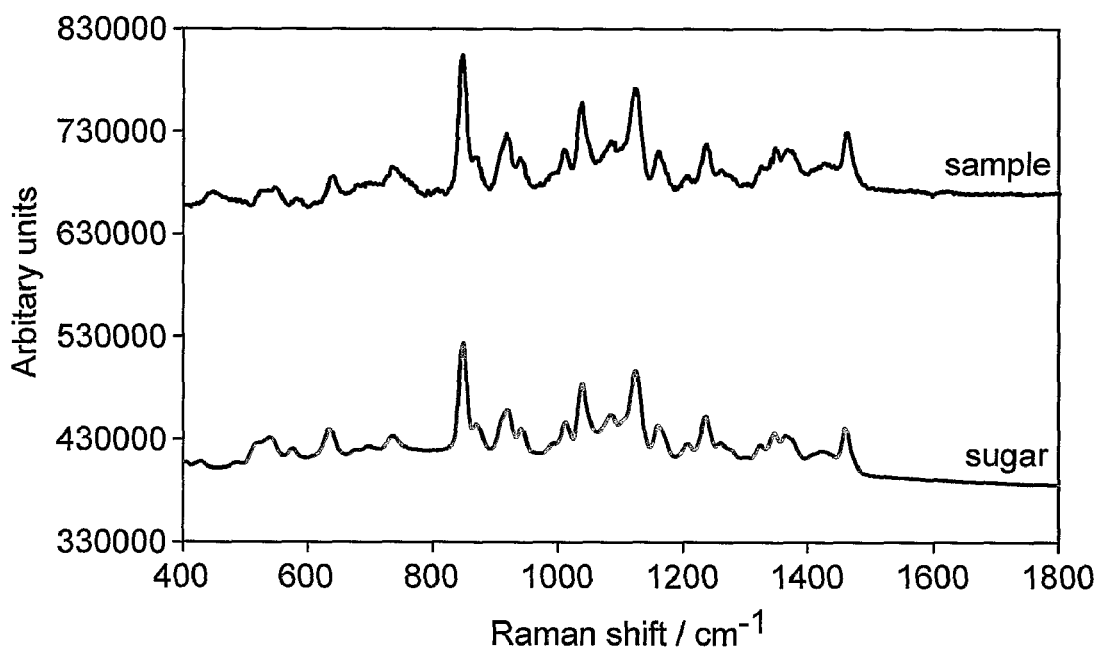
FIG. 6b shows the data of FIG. 6a corrected against the empty envelope and compared to a reference sample of sugar.

FIG. 6 shows spectra similar to those of FIG. 5, but in this instance brown envelopes were used. FIG. 6a shows two spectra, the first is a spectrum obtained from an empty envelope, and is labelled "blank". The second spectrum is from the brown envelope containing sugar. This spectrum is labelled "sample". For the brown envelope, the fluorescence background is much higher than for the white envelope, but additional features in the spectrum caused by the presence of sugar are clearly visible. FIG. 6b shows a background corrected spectrum of the sample along with a spectrum of sugar only. The features in the sample spectrum are very similar to those in the pure sugar sample evidencing that the package sample is highly likely to contain sugar.

The above described form of transmission Raman is useful for screening envelopes and packages for a wide range of chemicals. Reference spectra of hazardous chemicals would be stored in an analyser and the wavenumber or Raman shift at which each of the peaks occur would be stored in said analyser. Hence, the analyser would be configured to detect the presence of hazardous chemicals present in packages and envelopes. The above described embodiments could be improved to have increased screening rates by increasing laser power and reducing detection limits.

Spatially Offset Raman Spectroscopy (SORS)

In an alternative embodiment a different configuration of Raman spectroscopy may be used to identify and locate hazardous materials contained in packages or carried on a person. This technique is known as spatially offset Raman spectroscopy.

Technique

Figure 7:
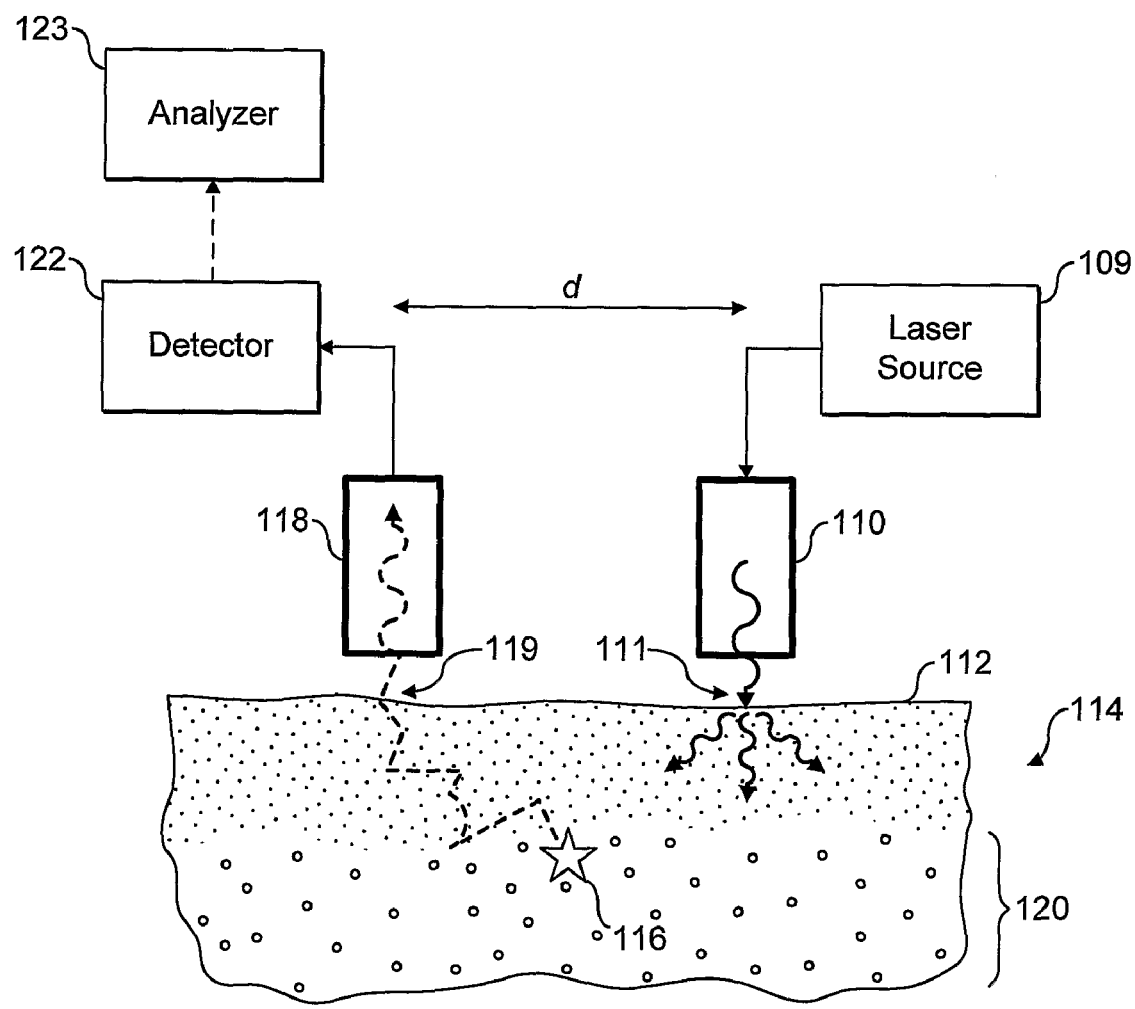
FIG. 7 is a schematic illustration of an arrangement for performing spatially offset Raman analysis on a package or envelope.

Referring now to FIG. 7 this alternative embodiment is shown in operation, in schematic cross section. A light source 110, incorporating or supplied by laser 109, is used to irradiate a localised entry region 111 of a surface 112 of a sample 114. The incident radiation from the light source is scattered diffusely through the sample. Some of the radiation may be absorbed by the sample, some may give rise to optical emissions for example by fluorescence, and some re-emerges unchanged through the sample surface 112.

A small proportion of the photons of the incident radiation are inelastically scattered giving rise to Raman photons, for example as illustrated by Raman event 116. The Raman photons in turn are diffusively scattered through the sample. Some may be absorbed, for example giving rise to fluorescence, but some emerge unchanged through the surface 112 to be collected at collector 118. The likelihood of a Raman photon undergoing a second Raman event is very small.

The collected light is analysed, for example using filters or a spectrometer, and a suitable sensor in detector 122, and the determined Raman spectra or spectral features are used further in analyzer 123, which is typically a computer. The detector may use a Fourier transform rather than a conventional dispersive spectroscopic technique.

Typically, most Raman photons will be generated close to the light source 110, where the incident radiation is most intense. These Raman photons can best be detected by collecting light at the light source 110, for example by using optics common with the light source. As distance from the light source increases, however, the intensity of Raman photons originating near the light source falls away more quickly than the intensity of Raman photons originating further away from the light source, especially from deeper within the sample. Preferential sampling of Raman photons from deeper within the sample can therefore be achieved by spacing the location at which light is collected from the location at which the sample is illuminated, and an analysis of how the detected spectral features change with spacing can provide more detailed sub-surface information.

In FIG. 7 Raman event 116 occurs in a subsurface layer 120. The spacing d between the light source 110 and the collector 118, or equivalently between an entry region 111 and a collection region 119 can be adjusted to select for a particular depth. In preferred embodiments, however, light is collected at a range of two or more spacings d, and an analyzer 23 is used to infer depth dependent characteristics of the sample from the Raman features of the collected and analyzed light for different values of d, which are spectrally analyzed by analyzer 22. One of the spacings could be at, or very close to the entry region.

Alternatively, if the spacing between the light source 110 and collector 118 is greater than the thickness of the sample, then the detected Raman scattered light will be a convolution of the spectra of the various materials in the sample. For example, if the sample is thin such as an envelope, package or an object wrapped in clothing, the spectra obtained will be a convolution of the spectra of the materials involved.

The incident irradiation and collection of light at a single, at multiple, or at a variable spacing can be achieved using a variety of geometries. For example, a single illumination region surrounded by an annular collection region may be used. Alternatively, linearly arranged collection points may be used.

In simplistic embodiments a single entry region may be provided by a single optical fibre brought close to the sample surface, and multiple collection regions may be provided by a linear array of collection fibres. Optical fibres may be similarly used to provide annular and other configurations of single and multiple fixed spacings and various mechanical arrangements may be used to provide variable spacings.

Experimental Example

In an experimental arrangement, the sample was a quartz cuvette wrapped in two and four layers of fabric respectively. The fabric used was an ordinary kitchen cloth 0.22 mm in thickness. The fabric colour was white with a green, pink, blue and yellow chequered pattern. A quartz cuvette is used as this does not exhibit Raman scattering at frequencies of interest.

The optical beam was generated in substantially the same way as the above described transmission embodiment, namely by use of an 827 nm laser beam that was spectrally purified using two angled 830 nm bandpass filters. However, in the present embodiment the beam diameter at the sample was 0.5mm.

Detection of Raman scattered light also uses broadly the same equipment as the above described transmission Raman embodiment. There is used a 1.2 f-number collection lens. However, in the present case the collection point is on the same surface as, but spaced away, from the illumination point (refer to FIG. 7). The results that follow were obtained using a separation between the illumination point and collection point of 5 mm. The collection optics also used 1:1 magnification to collect the scattered light into a 22 fibre probe. A combination of notch and edge filters were used to suppress the elastically scattered component of light. The Raman light was propagated through the 2 m long fibre system to a linear fibre and oriented vertically and placed in the input image plane of a Kaiser Optical Technologies Holospec spectrograph with an f-number of 1.4 NIR.

Raman spectra were collected using a deep depletion thermoelectrically cooled CCD camera (Andor technology, DU420A-BR-DD, 1024×256 pixels) by binning the signal from all the 22 fibres into one Raman spectrum. Hence, the Raman spectra were not corrected for the variation of detection system sensitivity across the detected spectral range.

Figure 8A:
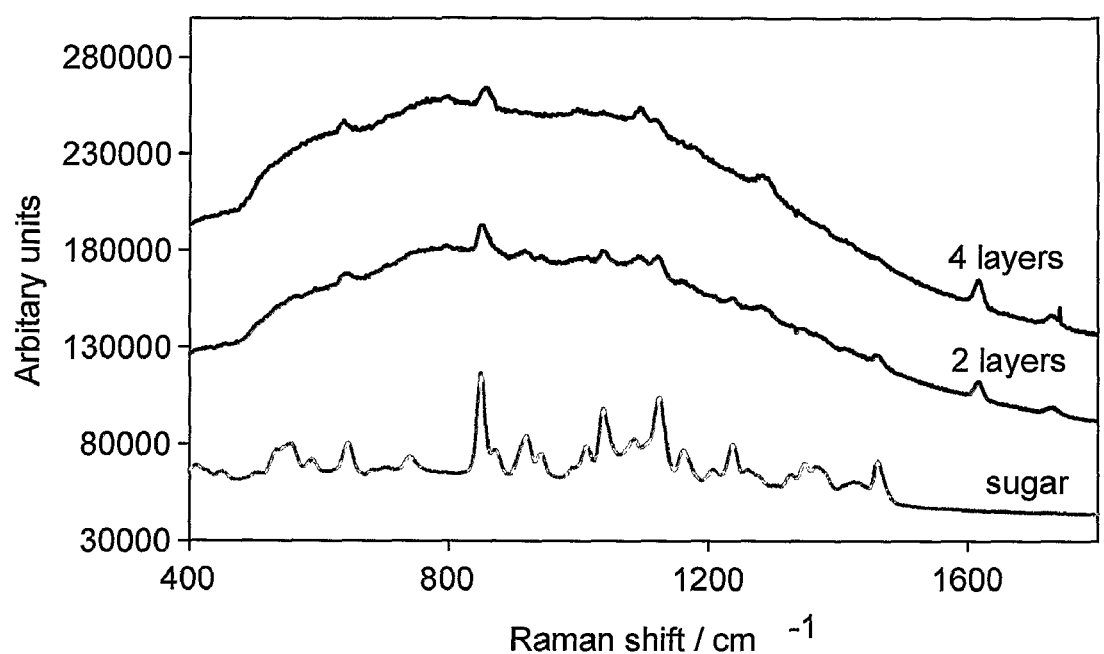
FIG. 8a shows spatially offset Raman spectra obtained from a cuvette of sugar wrapped in 2 or 4 layers of fabric and is compared to the spectrum for a reference sample of sugar. The spectra were obtained over an acquisition time of 10 seconds.
Figure 8B:
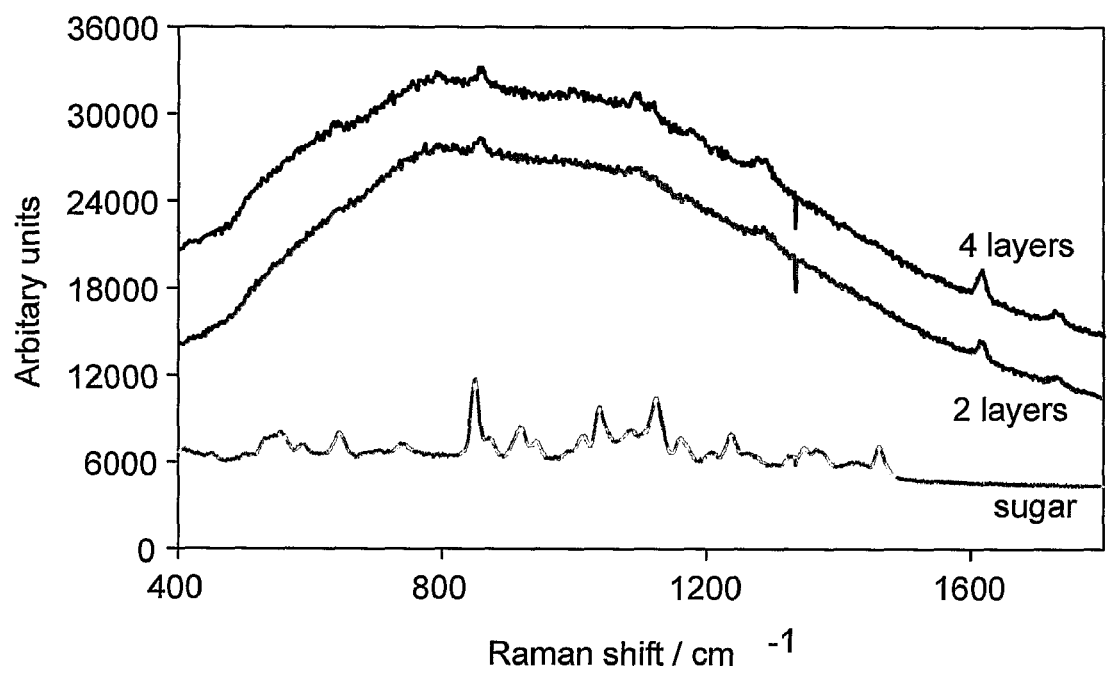
FIG. 8b shows data from the same samples as FIG. 8a and using the same technique but with an acquisition time of 1 second.
Figure 9:
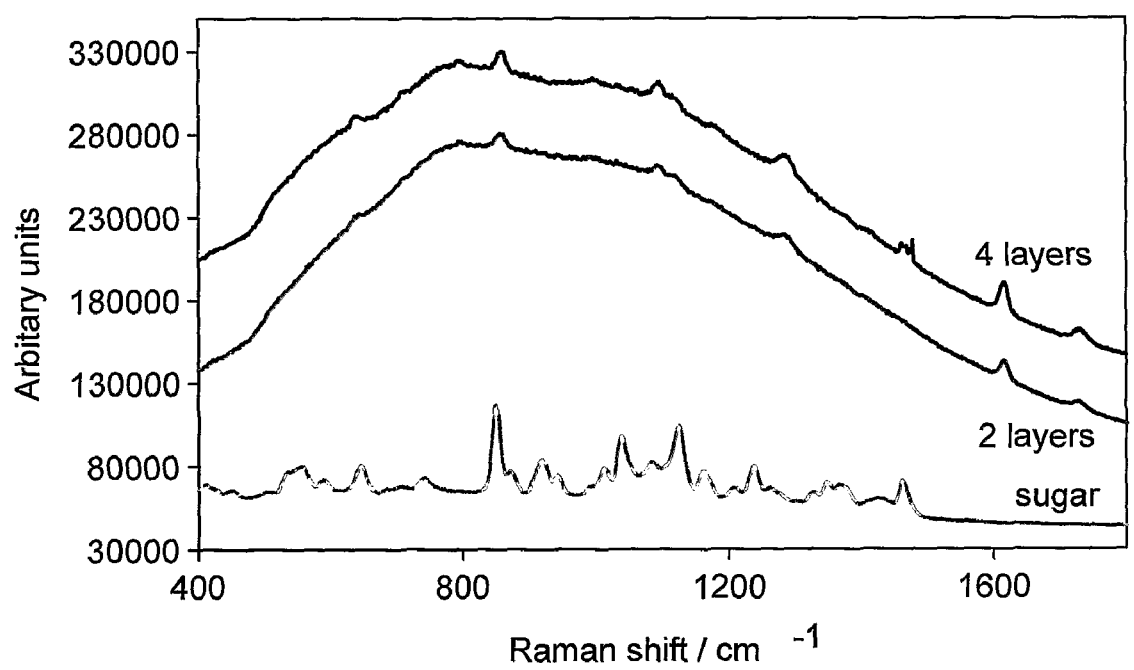
FIG. 9 shows spatially offset Raman spectra obtained from a cuvette of sugar placed in a brown envelope and then wrapped in 2 or 4 layers of fabric and is compared to the spectrum for a reference sample of sugar. The spectra were obtained over an acquisition time of 10 seconds.

FIGS. 8 and 9 show spectra obtained using the configuration described above. In particular, FIGS. 8a and 8b show spectra obtained of a sugar sample wrapped in two or four layers fabric. A spectrum of sugar alone is also shown. The difference between FIG. 8a and FIG. 8b is that the acquisition time for the former was 10 seconds, whereas for the latter was reduced to 1 second.

In FIG. 8a, features in the spectrum of the sugar wrapped in layers of fabric are clearly comparable to those of the spectrum of sugar. The spectra in FIG. 8b less clearly show features that may identify the substance present as the one second acquisition time has resulted in a much noisier spectrum. Nevertheless, the presence of sugar is still identifiable.

FIG. 9 shows results obtained when the cuvette of sugar was placed into a brown envelope before being wrapped in fabric. This not only adds to the thickness of the sample being analysed, but also increases the number of chemical species present thereby potentially influencing fluorescence interference. In fact, we have shown above in relation to transmission Raman spectroscopy that brown envelopes exhibit a relatively broad intense fluorescence in the Raman spectrum. The resulting analysis of the sugar placed in a brown envelope and then wrapped in two of four layers of fabric is shown in FIG. 9. Also shown is a spectrum of sugar only. The Raman features resulting from the sugar are clearly identifiable and not seriously obscured by the presence of the fabric or envelope.

The above described form of offset Raman is thus also useful for non-invasive detection and identification of hidden hazardous substances. Again reference spectra of hazardous chemicals could be stored in an analyser and the number and Raman shift at which each of the peaks occur would be stored in said analyser. Hence, the analyser would be configured to detect the presence of known hazardous chemicals present in packages, envelopes, or under clothing. The above described embodiments could be improved to have. increased screening rates by increasing laser power and reducing detection limits.

The above described embodiments show that Raman spectroscopy can be used for detection of hazardous substances. The embodiments may also be useful for detecting classes of substances having a characteristic signature, such as nitrides or amine groups. In addition, embodiments could be configured to recognise illegal substances such as drugs of abuse (e.g. heroine or cocaine) and counterfeit pharmaceuticals. It will be appreciated that various modifications may be made to the above embodiments while still falling within the scope of the claims. For example, other detection means, laser wavelengths and powers, and scanning rates may be used.

The invention claimed is:

1. A method of screening an object to identify the presence or absence of one or more predefined substances or classes of substances, the method comprising the steps of:
   supplying incident radiation to an incident region on a surface of said object;
   detecting Raman scattered light from a collection region on a surface of said object, the collection region being spaced from the incident region;
   comparing the Raman scattered light to information related to said predefined substances or classes of substances; and
   determining the presence or absence of said one or more predefined substances or classes of substances in said object.

2. The method of claim 1, wherein the incident region is on a first surface of the object, and the collection region is on a second surface of the object opposed to said first surface.

3. The method of claim 2, wherein the incident region on the first surface and the collection region on the second surface are aligned to an axis of the object.

4. The method of claim 1, further comprising detecting Raman radiation backscattered from said first surface.

5. The method of claim 1, wherein the incident region and the collection region are on the same surface.

6. The method of claim 5, wherein the step of detecting at a collection region is performed at a plurality of spacings from said incident region.

7. The method of claim 6, wherein the steps of comparing and determining include associating the presence or absence of said one or more predefined substances or classes of substances in said object with different depths within the object.

8. The method of claim 1, wherein the information related to the predefined substances or classes of substances is stored in a database.

9. The method claim 1, wherein the object is an envelope or package.

10. The method of claim 1, wherein the object is a garment of clothing.

11. The method of claim 1, wherein the one or more predefined substances or classes of substances are hazardous.

12. The method of claim 1, wherein the one or more predefined substances or classes of substances are toxic.

13. The method of claim 1, wherein the one or more predefined substances or classes of substances are explosive.

14. The method of claim 1, wherein the one or more predefined substances or classes of substances are illegal substances.

15. The method of claim 1, wherein the incident radiation is generated using one or more lasers.

16. Screening apparatus for identifying the presence or absence of predefined substances or classes of substances in an object, the apparatus comprising:
   illumination optics arranged to direct incident radiation at an incident region on the surface of said object;
   collection means for collecting Raman scattered light from a collection region on the surface of said object, the collection region being spaced from the incident region;
   a comparator for comparing the Raman scattered light to information related to said predefined substances or classes of substances; and
   an analyser for determining the presence or absence of said one or more predefined substances or classes of substances in said object.

17. The apparatus of claim 16, wherein the incident region is on a first surface of the object, and the collection region is on a second surface of the object opposed to said first surface.

18. The apparatus of claim 17, wherein the incident region on the first surface and the collection region on the second surface are aligned to an axis of the object.

19. The apparatus of claim 16, further comprising a second collections means for collecting Raman radiation backscattered from said first surface.

20. The apparatus of claim 16, wherein the incident region and the collection region are on the same surface.

21. The apparatus of claim 20, wherein the collecting means is adapted to collect Raman scattered radiation at a plurality of spacings from said incident region.

22. The apparatus of claim 21, wherein the presence or absence of said one or more predefined substances or classes of substances is associated with different depths within the object.

23. The apparatus of claim 16, further comprising a database for storing the information related to the predefined substances or classes of substances.

24. The apparatus of claim 16, wherein the object is an envelope or package.

25. The apparatus of claim 16, wherein the object is a garment of clothing.

26. The apparatus of claim 16, wherein the one or more predefined substances or classes of substances are hazardous.

27. The apparatus of claim 16, wherein the one or more predefined substances or classes of substances are toxic.

28. The apparatus of claim 16, wherein the one or more predefined substances or classes of substances are explosive.

29. The apparatus of claim 16, wherein the one or more predefined substances or classes of substances are illegal substances.

30. The apparatus of claim 16, wherein one or more lasers are used to generate the incident radiation.

* * * * *